United States Patent [19]
Levius et al.

[11] Patent Number: 5,662,582
[45] Date of Patent: Sep. 2, 1997

[54] EVERTING INCONTINENCE PLUG

[75] Inventors: Dezso K. Levius, Bloomington; David W. Anderson, Maple Grove, both of Minn.

[73] Assignee: Iotek, Inc., Minneapolis, Minn.

[21] Appl. No.: 394,459

[22] Filed: Feb. 27, 1995

[51] Int. Cl.$^6$ ................................................ A61F 2/00
[52] U.S. Cl. ................................ 600/29; 128/DIG. 25
[58] Field of Search ................. 600/29–32; 128/DIG. 25

[56] References Cited

U.S. PATENT DOCUMENTS

| | | | |
|---|---|---|---|
| 2,494,393 | 1/1950 | Lamson | 600/29 |
| 2,564,399 | 8/1951 | Franken | 600/32 |
| 3,421,509 | 1/1969 | Fiore . | |
| 3,506,011 | 4/1970 | Silverman . | |
| 3,646,929 | 3/1972 | Bonnar | 600/29 |
| 3,797,478 | 3/1974 | Walsh et al. . | |
| 3,841,304 | 10/1974 | Jones . | |
| 3,908,635 | 9/1975 | Viiek . | |
| 3,908,663 | 9/1975 | Viek . | |
| 4,109,659 | 8/1978 | Sheridan . | |
| 4,779,611 | 10/1988 | Grooters et al. . | |
| 4,950,223 | 8/1990 | Silvanov | 600/32 |
| 5,030,199 | 7/1991 | Barwick et al. . | |
| 5,082,006 | 1/1992 | Jonasson . | |
| 5,090,424 | 2/1992 | Simon et al. . | |
| 5,163,927 | 11/1992 | Woker et al. . | |

FOREIGN PATENT DOCUMENTS

| | | |
|---|---|---|
| 0 369 923 | 5/1990 | European Pat. Off. . |
| 0 444 831 | 9/1991 | European Pat. Off. . |
| 29 19 467 | 10/1980 | Germany . |

*Primary Examiner*—Lee S. Cohen
*Assistant Examiner*—John P. Lacyk
*Attorney, Agent, or Firm*—Merchant, Gould, Smith, Edell, Welter & Schmidt

[57] ABSTRACT

An incontinence treatment plug includes a plug member which is sized to extend in an extended position into a urethra in sealing engagement. The plug member is originally everted. A force is applied to the plug member to force the plug member from an everted position into an extended position.

1 Claim, 4 Drawing Sheets

5,662,582

1

EVERTING INCONTINENCE PLUG

I. BACKGROUND OF THE INVENTION

1. Field of the Invention

This invention pertains to an incontinence device. More particularly, this invention pertains to a female incontinence device for insertion into the urethra.

2. Description of the Prior Art

Female incontinence is a very common problem. Women suffering from incontinence experience a disruption in both their professional and recreational activities. Further, incontinence is detrimental to the self-esteem of the patient.

Incontinence control devices for insertion into the urethra are known in the prior art. Examples of such include those shown in U.S. Pat. Nos. 5,090,424 and 5,082,006. For a female incontinence device to be effective and to be used by a large number of patients, the design should accomplish several objectives. The device should restore continence to an acceptable level in a majority of patients for whom it may be prescribed. The incontinence device must be used with a minimum of complications. The more serious complications include U.T.I. and hematuria. The incontinence device should be insertable into the urethra by the patient with a minimum of physical and social discomfort. Also, the incontinence device must be designed in such a manner and with materials acceptable to the Food and Drug Administration, so the device can be produced, packaged and sterilized at low cost.

Commonly assigned U.S. patent application Ser. No. 08/328,331 filed Oct. 24, 1994, and entitled "Incontinence Device" by inventors Robert E. Buuck and Dezso K. Levius recognizes that insertion of a plug into the urethra can cause the transportation of bacteria or other pathogens along the urethra and toward or into the bladder. The aforementioned '331 application utilizes a sleeve for initial insertion into the urethra. The incontinence plug is then passed through the sleeve such that the distal end of the plug does not come in contact with the entrance to the urethra and cannot pick up pathogens or bacteria to be transported along the length of the urethra.

While the aforementioned devices advance treatment of incontinence, a continued improvement in incontinence devices is desired. It is an object of the present invention to provide an improved design of an incontinence plug.

II. SUMMARY OF THE INVENTION

According to a preferred embodiment of the present invention, an everting incontinence plug is provided. The plug includes a housing with a plug member secured to the housing. The plug member is sized to extend from the housing in an extended position into a urethra in sealing engagement. The plug member is secured to the housing in an everted position prior to insertion into the urethra. A force is applied to the plug member in the everted position for the plug member to extend to the extended position in response to the force.

III. BRIEF DESCRIPTION OF THE DRAWINGS

2

Figure 3:
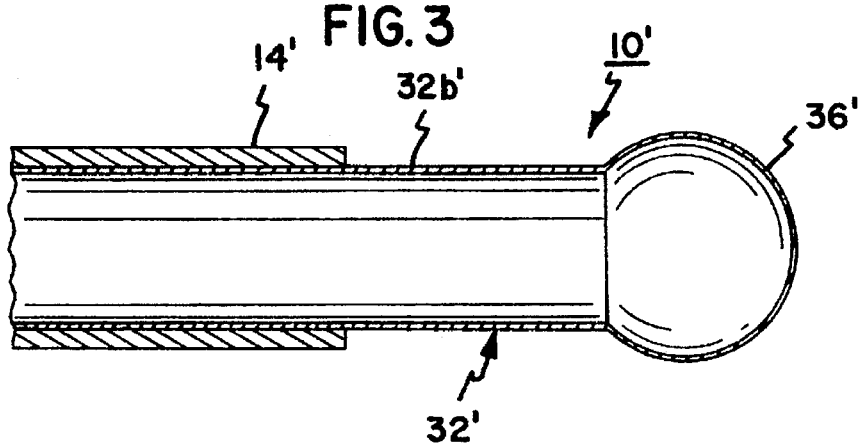
Figure 4:
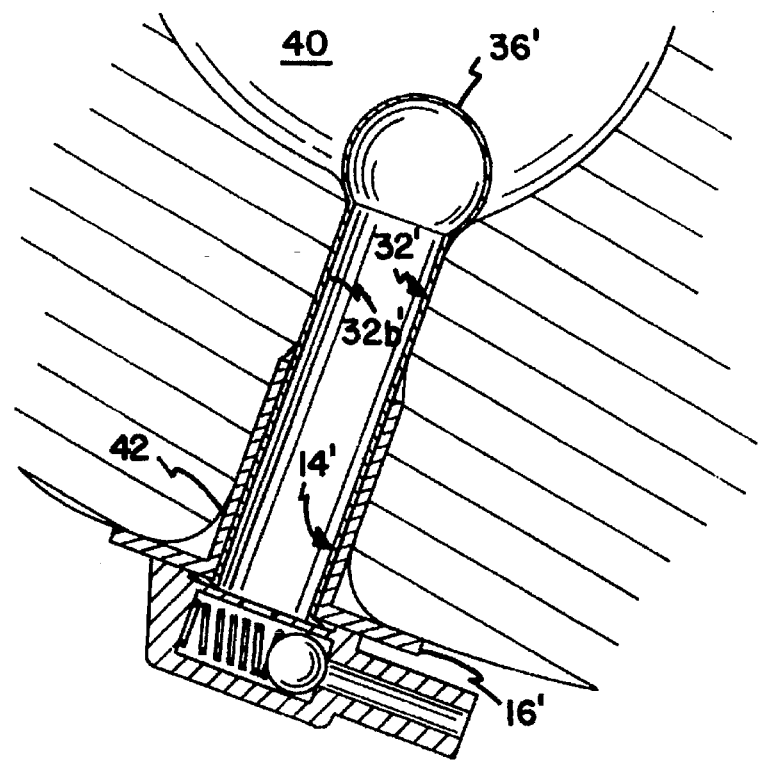
Figure 5:
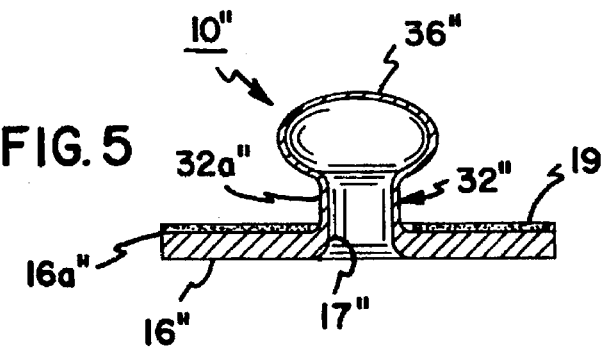
Figure 6:
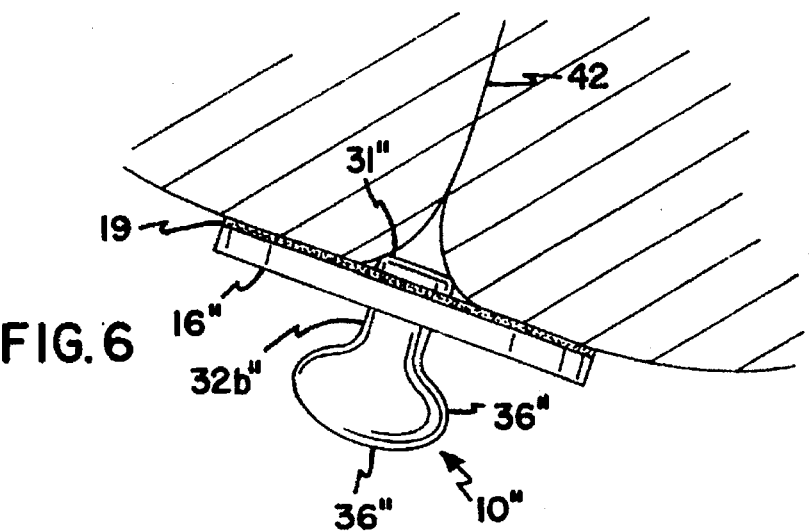
Figure 7:
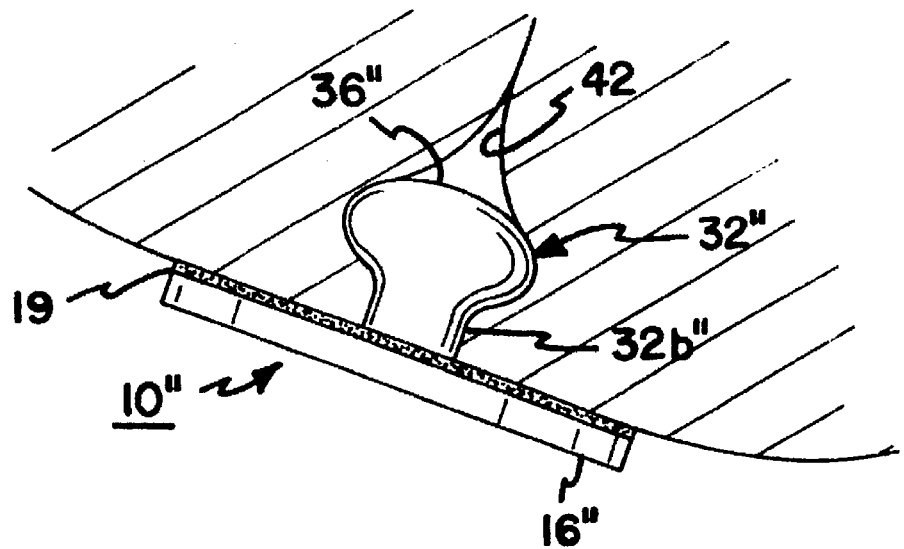
Figure 5A:
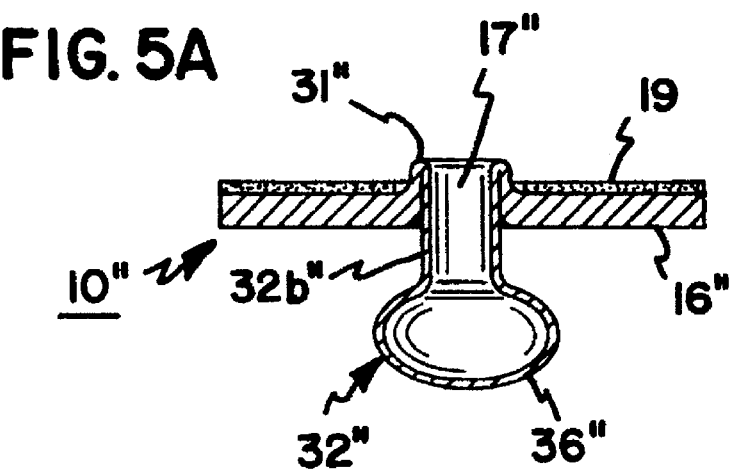

FIG. 3 is a side sectional view of a plug member according to an alternative embodiment of the present invention where a distal end of the plug member is a balloon member portion;

FIG. 4 shows the plug of FIG. 3 in sealing engagement within a urethra and bladder;

FIG. 5 shows an alternative embodiment of a plug in cross-section with the plug member shown in an extended position;

FIG. 5A is the view of FIG. 5 showing a plug member in an everted position;

FIG. 6 shows the plug of FIG. 5 in an everted position and positioned against a urethral meatus prior to insertion of the plug member into the urethra;

FIG. 7 is the view of FIG. 6 showing insertion of the plug from an everted to an extended position into the urethra.

IV. DESCRIPTION OF THE PREFERRED EMBODIMENT

With reference now to the various drawing figures in which identical elements are numbered identically throughout, a description of the preferred embodiment of the present invention will now be provided.

Figure 1:
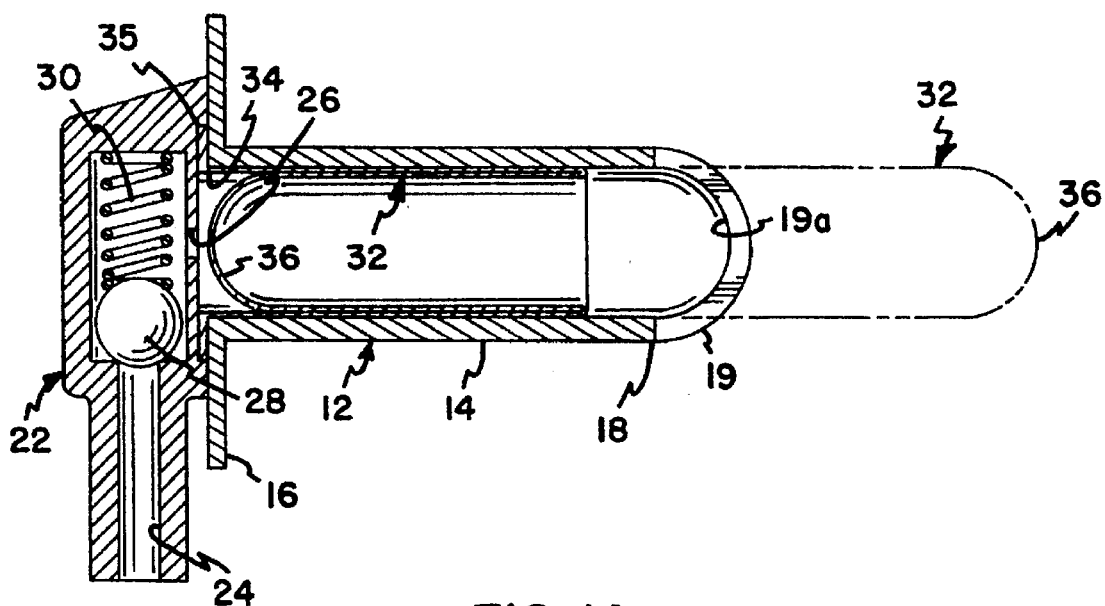
FIG. 1 is a side sectional view of an everting plug according to the present invention with a plug member shown in an everted position in solid lines and in an extended position in phantom lines.
Figure 1A:
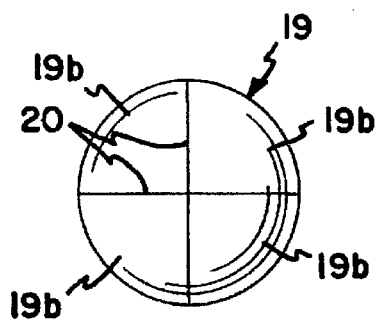
FIG. 1A is an end elevation view of the plug of FIG. 1.

With initial reference to FIG. 1, an everting plug 10 is shown having a soft polymeric housing 12 which includes a hollow cylindrical portion 14 and a radially extending flange 16 at one end of the cylindrical portion 14. An opposite end 18 is domed with a hemispherical dome 19. FIG. 1A is an elevation view of the dome 19 and is shown with a pair of cuts 20 formed through the dome 19 at right angles. Accordingly, an object forced against the dome 19 on its inner surface 19a can protrude through the dome 19 since the cuts 20 will permit the four elements 19b of the dome 19 to spread apart.

A valve assembly 22 is secured to the flange 16. The valve assembly 22 has a fluid inlet 24 and a fluid outlet 26. Outlet 26 communicates with the interior of the cylindrical portion 14. A check valve 28 is positioned within the valve assembly 22 and urged against the inlet passage 24 in sealing engagement by means of a spring 30. With valve assembly 22, a fluid (such as air) can be admitted into the inlet passage 24 under pressure through any suitable means (for example, by a syringe) with a fluid pressure urging the check valve 28 to move against the bias of the spring 30 to permit a pressurized fluid to pass through the outlet 26 into the interior of the cylindrical portion 14.

A flexible elastic plug member 32 is secured to the housing 12. The plug member 32 is generally tubular and has an open proximal end 34 and a closed distal end 36. The open proximal end 34 has a flange 35 received with a groove defined by opposing surfaces of valve assembly 22 and flange 16.

In FIG. 1, the plug member 32 is shown in an everted position with the distal end 36 disposed rearwardly from end 18 (i.e., towards valve assembly 22). Admission of pressurized fluid from valve assembly 22 into the cylindrical portion 14 causes the plug member 32 to move from the everted position shown in solid lines in FIG. 1 to the extended position shown in phantom lines in FIG. 1. Namely, the pressurized fluid admitted to the interior of the cylindrical portion 14 causes the plug member 32 to extend outwardly forcing the distal end 36 through the dome 19. In a preferred embodiment, the full length (i.e., length from end 34 to extended end 36) of the extended plug portion 32 is approximately equal to twice the full length of the cylindrical portion 14.

The extension of the plug member 32 is shown best in FIGS. 2A–2E. In FIGS. 2A–2E, the dome 19 is not shown for purposes of clarity.

Figure 2A:
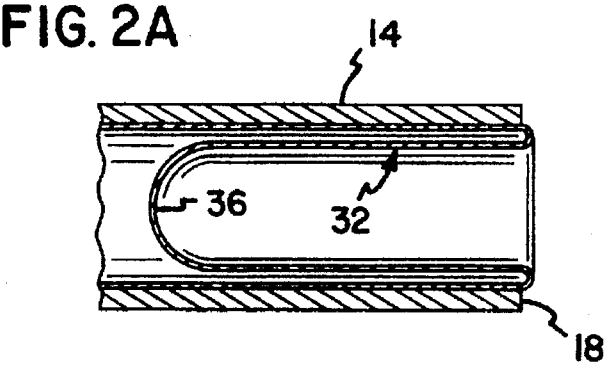
FIGS. 2A–2E show the plug member of FIG. 1 progressively being extended from an everted position to a fully extended position.
Figure 2B:
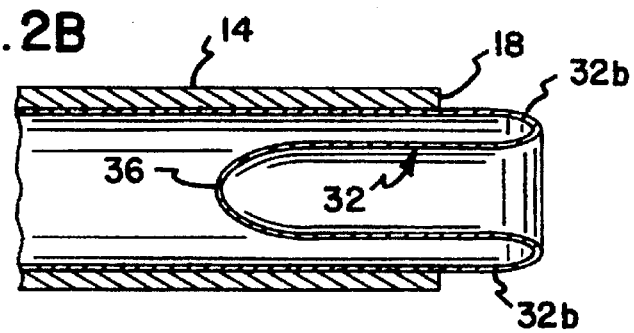
Figure 2C:
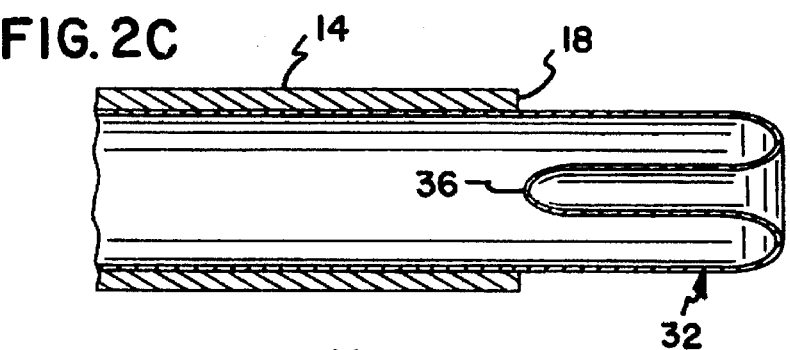
Figure 2D:
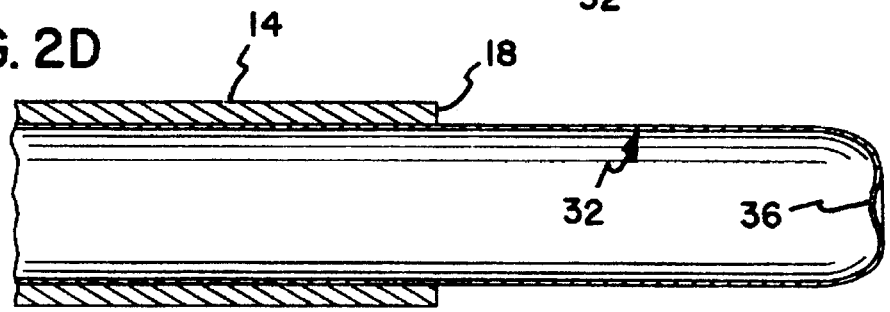
Figure 2E:
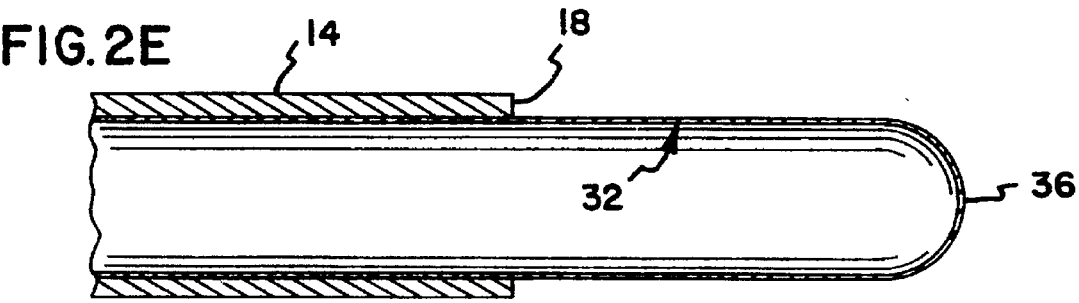

In FIG. 2A, the plug member 32 is shown in an everted position. Upon admission of a pressurized gas into the cylinder 14, the gas surrounds the plug member 32 occupying a space defined between opposing surfaces of the plug member 32 and the cylinder 14. This causes the cylindrical wall 32b (FIG. 2B) of the plug member 32 nearest proximal end 34 to be the first portion of the plug member 32 to be urged out of cylinder 14 as illustrated in FIG. 2B. Continued application of pressure to the interior of cylinder 14 causes further extension of plug member 32 until the plug member 32 achieves a fully extended position as shown in FIG. 2E. It should be noted in FIGS. 2A–2E that the proximal end 36 of the plug member 32 is the last portion of the plug member 32 to be extended.

In a preferred embodiment, the cylindrical member 14 has an axial length equal to approximately one half of the length of a urethra of a patient for whom the plug 10 is intended for use. In an adult female urethra, a typical urethra would be about 35 millimeters long. Accordingly, for such a patient the axial length of cylindrical member 14 is 17 millimeters. Also, the diameter of the cylindrical member 14 is selected to be about 6 millimeters.

After insertion of the cylindrical member 14 into the urethra with flange 16 abutting the patient at the meatus and preventing further insertion of the cylindrical member into the urethra, pressurized fluid is admitted into the cylindrical member 14 through the valve assembly 22 causing the plug member 32 to move from the everted into the extended position. As the plug member 32 moves to the extended position, it advances past the sphincter muscles of the urethra and seals against the urethra wall to prevent fluid flow through the urethra.

With the structure thus described and with the method by which the plug 32 extends with the distal end 36 of the plug being the last portion of the plug to achieve a fully extended position, the distal end 36 does not transport pathogens across the length of the urethra. Accordingly, the present invention provides effective sealing without transportation of pathogens. Further, since the everting plug member 32 is progressively folding outwardly, no portion of the plug member 32 is sliding relative to the urethra as is common with prior art plugs which are forced into the urethra. The absence of sliding movement of the material of the plug member 32 relative to the urethra wall prevents trauma to the urethral wall which could otherwise occur by reason of relative movement between the urethral wall and a plug. Further, the everting nature of the plug member 32 and the absence of relative sliding movement of the plug member 32 relative to the urethral wall results in increased comfort experienced by the patient by reason of use of the plug 10 of the present invention.

FIG. 3 shows an alternative embodiment of the present invention. In FIG. 3, a plug member 32' is shown secured to a cylindrical member 14'. The plug member 32' differs from the plug member 32 only in that the distal end 36' of the plug member 32' is provided with a thinner elastic wall than the tubular portion 32b' of the plug member 32'. Accordingly, when pressurized fluid is admitted into the interior of the cylindrical member 14', the distal end 36' of the plug member 32' expands outwardly to a diameter greater than the diameter of tubular portion 32b'. With the modification of FIG. 3, the plug member 32' is selected to have a length such that the expanding distal end 36' is positioned at the bladder neck and within the bladder after full insertion of the plug 10'. This is illustrated in FIG. 4 where the ballooned distal end 16' is positioned within the bladder 40 and with the main body 32b' of the plug 32' and with the cylindrical portion positioned within the urethra 42 and with the flange 16' abutting the entrance to the urethra 42. The use of an expanding distal end 36' securely anchors the plug 10' within the urethra as well as providing additional sealing by reason of the expanded end 36' at the bladder neck.

The embodiments of the present invention discussed thus far utilize a fluid pressure to extend the plug member from an everted position into an extended position. However, mechanical force may be applied to achieve the same extension of an everted plug. Such an embodiment is shown in FIGS. 5–7. In FIG. 5, a plug 10" includes a flange 16" having a central opening 17". The flange 16" is integrally molded with a thin walled plug 32" having a tubular portion 32b" (surrounding opening 17") and an enlarged distal end 36". The surface 16a" of the flange 16" to be opposing and surrounding the meatus is provided with an adhesive 19 to adhere the flange 16 against the patient's body. Prior to insertion into the urethra, the plug 36" is everted into itself through opening 17" as shown in FIG. 5A. The eversion results in a portion 31" of tubular portion 32b" extending beyond surface 16a". This protruding portion 31" permits positioning of the plug 10" with the portion 31" extending into the meatus and with the flange 16" adhered to the patient as shown in FIG. 6. The patient then inverts the button 36" by pushing it through opening 17" into the extended position shown in FIG. 7. The expanded portion 36" seals in the bladder 40 at the urethral entrance to the bladder 40. An alternate embodiment to FIGS. 5–7 is to have adhesive on the exterior of enlarged end 36" to adhere to the urethral wall.

With each of the embodiments of the plug shown and described above, an everting incontinence plug has been provided. The everting incontinence plug permits ease of use and insertion as well as minimizing the transportation of pathogens along the urethra and minimizing discomfort to the patient and trauma to the urethra wall. While the invention has been disclosed in preferred embodiments for the purpose of illustration, it will be appreciated that modifications and equivalents of the disclosed concepts may be apparent to those skilled in the art having the benefit of the teachings of the present invention. It is intended that the scope of the present invention not be limited by the specific embodiments shown above but shall include such modifications and equivalents.

What is claimed is:

1. A plug for treating incontinence comprising:

a stop means for limiting insertion at the meatus of a urethra; and a plug member secured to said stop means and sized to extend therefrom in an extended position into a urethra in sealing engagement, said plug member sized to have substantially the same length and width as the urethra when said plug member is in said extended position;

said plug member secured to said stop means in an everted position and responsive to a force for said plug member to extend from said everted position to said extended position in response to said force;

a housing having a top portion and having an inner surface defining a hollow cylindrical area, said plug member contained within said housing when said plug member is in said everted position; and said top portion is domed with at least one incision such that said plug member is forced through said top portion in response to said force, said plug member extending axially through said housing when said plug member is in said extended position.

* * * * *

UNITED STATES PATENT AND TRADEMARK OFFICE
CERTIFICATE OF CORRECTION

PATENT NO. : 5,662,582

DATED : September 2, 1997

INVENTOR(S) : Dezso K. Levius et al.

It is certified that error appears in the above-identified patent and that said Letters Patent is hereby corrected as shown below:

In column 3, line 65, please insert --14'-- after the word "portion".

Signed and Sealed this

Second Day of June, 1998

*Attest:*

BRUCE LEHMAN

*Attesting Officer*  *Commissioner of Patents and Trademarks*